(12) United States Patent
Rovinski et al.

(10) Patent No.: US 6,572,863 B1
(45) Date of Patent: *Jun. 3, 2003

(54) CONSTITUTIVE EXPRESSION OF NON-INFECTIOUS HIV-LIKE PARTICLES

(75) Inventors: Benjamin Rovinski, Thornhill (CA); Fei-Long Yao, Toronto (CA); Shi Xian Cao, Etobicoke (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/555,834

(22) PCT Filed: Dec. 14, 1998

(86) PCT No.: PCT/CA98/01164

§ 371 (c)(1),
(2), (4) Date: Jul. 19, 2000

(87) PCT Pub. No.: WO98/44788

PCT Pub. Date: Oct. 15, 1998

Related U.S. Application Data

(60) Substitute for application No. PCT/CA98/01164 on Dec. 14, 1998, which is a continuation of application No. 08/991,773, filed on Dec. 16, 1997, now Pat. No. 6,121,021.

(51) Int. Cl.$^7$ .................. A61K 48/00; A61K 39/21; C07H 21/02; C12N 15/867; C12N 15/63

(52) U.S. Cl. .................. 424/208.1; 424/93.1; 424/93.2; 424/93.6; 424/204.1; 424/207.1; 435/320.1; 435/235.1; 435/236; 435/325; 435/366; 435/455; 435/456; 435/91.4; 435/91.41; 435/91.42; 514/2; 514/44; 536/23.1; 536/23.72; 536/24.1

(58) Field of Search .................. 435/320.1, 235.1, 435/236, 325, 366, 455, 456, 91.4, 91.41, 91.42; 536/23.1, 23.72, 24.1; 424/93.1, 93.2, 93.6, 204.1, 207.1, 208.1; 514/2, 44

(56) References Cited

U.S. PATENT DOCUMENTS

| | | |
|---|---|---|
| 5,439,809 A | 8/1995 | Haynes et al. |
| 5,571,712 A | 11/1996 | Haynes et al. |
| 5,674,984 A | 10/1997 | Berman et al. |
| 6,121,021 A * | 9/2000 | Rovinski et al. ........... 435/69.3 |

OTHER PUBLICATIONS

Vicki Glaser, Biotech Firms Shift Focus Toward Therapeutic HIV Vaccine Development, GENETIV Engineering News Jan. 1, 1996.*
World Health Organization, 1996. Wkly Epidemiol. Rec. 48:361.
Haynes B. F., Pantaleo G., Fauci A.S. 1996. Science 271:324–328.
Bryson Y.T., Pang S., Wei L.S. et al. 1995. N. Engl. J. Med. 332:833–834.
Rowland–Jones S., Sutton J., Ariyosh K., et al. 1995. Nat. Med. 1:59–64.
Pincus S., Messer K. G., Nara T.L., et al. 1994. J. Clin. Invest. 93:2508–2513.
Hogervorst E., Jurrians S., de Wolf F., et al. 1995. J. Infect. Dis. 171:811–821.
Markham R. B., Coberly j., Ruff A.J., et al. 1994. Lancet 343:1364.
Moore J.P. 1995. Nature 376:115.
Chapman, B.S. et al. 1991. Nucleic Acids Res. 19:3979–3986.
Yao F–L., Klein M. H., Loosmore S., Rovinski B. 1995, Bio Techniques 18:372–376.
Wain–Hobson S., Sonigo P., Danos O., Cole S., Alizon M. 1985. Cell 40:9–17.
Igarashi T. et al; Journal of General Virology: 1997 78: 985–989—XP–0–02105303.
Desrosiers Ronald C.—Aids Research and Human Retroviruses—vol. 8, No. 3. Jun. 8, 1992.
Chang Lung–ji et al; Virology 211, pp. 157–169 (1995); XP–002086308.

\* cited by examiner

*Primary Examiner*—David Guzo
(74) *Attorney, Agent, or Firm*—Sim & McBurney

(57) ABSTRACT

Non-infectious, non-replicating immunogenic HIV-like particles are produced by stable long-term constitutive expression in mammalian cells by eliminating elements toxic to the mammalian cells. An expression vector contains a nucleic acid molecule comprising a modified HIV genome devoid of long terminal repeats and wherein Tat and vpr sequences are functionally disabled and a constitutive promoter operatively connected to the modified HIV genome for constitutive expression of the modified genome to produce the HIV-like particles.

22 Claims, 4 Drawing Sheets

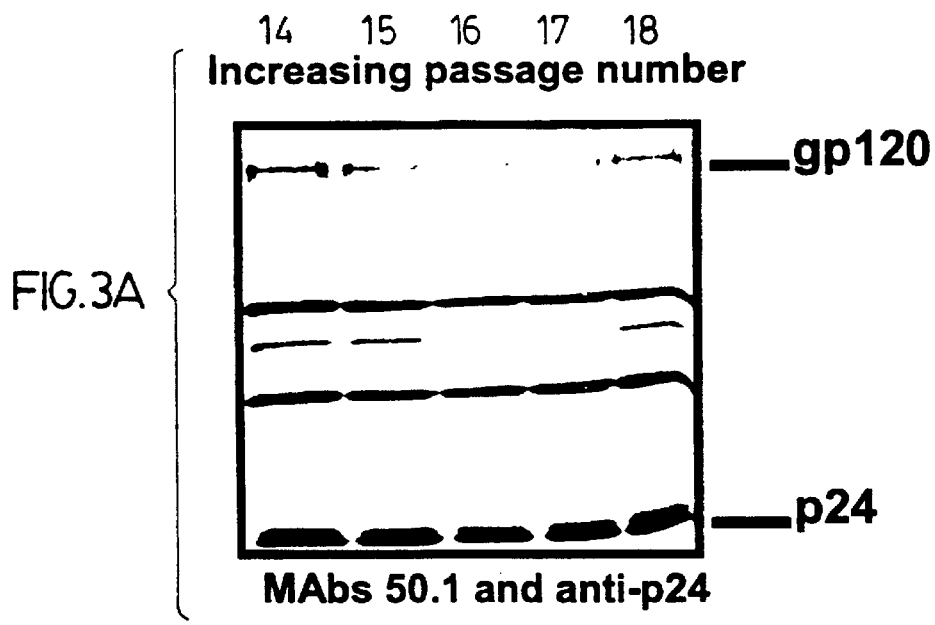
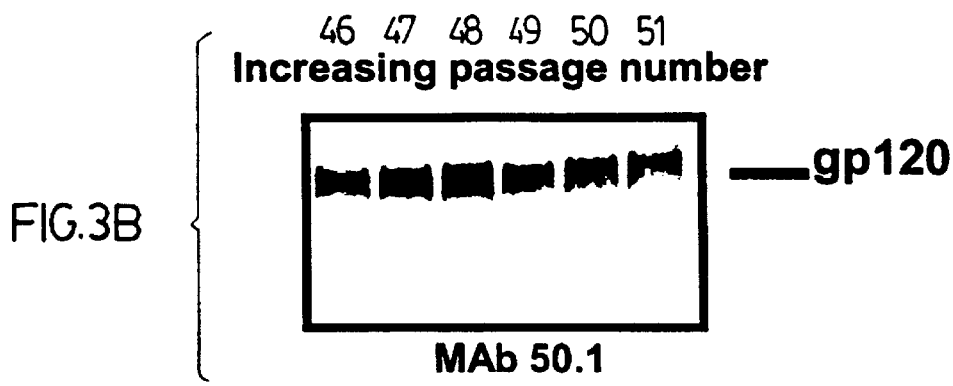
1. Mock Vero plus NaBu
2. Vero-356 plus NaBu
3. Mock Vero plus NaBu and Dexamethasone
4. Vero-356 plus NaBu and Dexamethasone
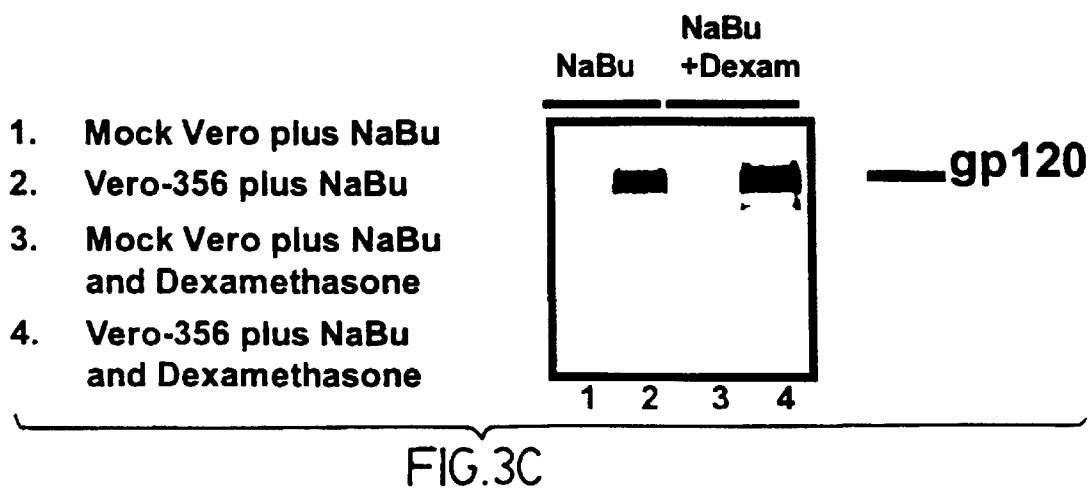

CONSTITUTIVE EXPRESSION OF NON-INFECTIOUS HIV-LIKE PARTICLES

REFERENCE TO RELATED APPLICATIONS

This application is a United States National Phase filing under 35 USC 371 of PCT/CA98/01164 filed Dec. 14, 1998 which is a continuation of U.S. patent application Ser. No. 08/991,773 filed Dec. 16, 1997 (now U.S. Pat. No. 6,121,021.

FIELD OF INVENTION

This invention relates to the expression of non-infectious, non-replicating immunogenic HIV-like particles and, in particular, to genetic modifications required to obtain long term high level constitutive expression of such particles.

BACKGROUND TO THE INVENTION

Human immunodeficiency virus is a human retrovirus and is the etiological agent of acquired immunodeficiency syndrome (AIDS). It is estimated that more than 18 million people have been infected with HIV as of mid 1996 (ref. 1—various references are referred to in parenthesis to more fully describe the state of the art to which this invention pertains. Full bibliographic information for each citation is found at the end of the specification, immediately preceding the claims. The disclosure of these references are hereby incorporated by reference into the present disclosure).

As the HIV-1 epidemic continues to spread world wide, the need for an effective vaccine remains urgent. Efforts to develop such a vaccine have been hampered by three main factors: (a) the extraordinary ability of the virus to mutate; (b) inability of most known specificities of anti-HIV antibodies to neutralise HIV primary isolates consistently; and (c) lack of understanding of the correlates of protective immunity to HIV infection. In view of the complex biology of HIV-host interactions, the most fruitful avenue may be development of multivalent HIV immunogens tailored to HIV isolates in specific geographical locations.

CD8 CTL that kill HIV-infected cells and antibodies that broadly neutralise HIV primary isolates might be protective anti-HIV immune responses in uninfected individuals who are subsequently exposed to HIV (ref. 2).

The definition of a successful preventative HIV immunogen is controversial. Protective anti-HIV immune responses may prevent HIV infection completely, may allow only transient infection, leading to clearance of virus, or may merely limit the extent of HIV infection, but in so doing prevent the development of AIDS. One suggestion is that clearance of HIV occasionally occurs after both maternal-fetal HIV transmission (ref. 3) and sexual transmission of HIV (ref. 4). Consequently, if protective anti-HIV immune responses could be induced by an immunogen in an HIV-uninfected person, protection might be achieved via early termination of HIV infection.

It has been shown that anti-recombinant (r) gp120 envelope antibodies raised in animals or in human volunteers neutralise HIV grown in laboratory-adapted T-cell lines but not primary isolates of the virus grown in peripheral blood mononuclear cells. This observation raises important questions about the roles of various spcificities of neutralising antibodies in protection against HIV. The predominant types of anti-HIV neutralising antibodies raised against gp120 are antibodies against the third variable (V3) region of gp120, as well as antibodies against the conformationally determined CD4 binding site centred around the fourth constant (C4) region of gp120. Although laboratory-adapted variants are pathogenic and have caused AIDS in man after laboratory accidents (ref. 5), the relevance of these variants in vivo in community-acquired infections is unknown. Serum concentrations of antibodies against the V3 gp120 region and of antibodies that neutralise laboratory-adapted HIV strains do not protect individuals from developing AIDS (ref. 6), nor do anti-V3 antibodies seem protective against maternal-fetal HIV transmission (ref. 7).

Thus, for induction by HIV immunogens of neutralising antibodies to prevent HIV infection, HIV immunogens are probably needed which are capable of inducing anti-HIV antibodies that neutralise both HIV laboratory-adapted isolates and HIV primary isolates grown in peripheral blood mononuclear cells (ref. 8).

There is suggestive evidence that envelope oligomers of HIV primary isolates may be appropriate immunogens for induction of anti-HIV neutralising antibodies against primary HIV isolates grown in peripheral blood mononuclear cells. Future studies are expected to focus on the envelope of HIV primary isolates as the target of neutralising antibodies. If HIV envelope oligomers are successful in inducing antibodies that neutralise HIV primary isolates, the neutralising antibody specificity may be variant specific and, if so, the issue of HIV variability would still need to be addressed.

Several candidate vaccines, based on different concepts, are at different stages in the HIV vaccine development pipeline. Candidate vaccines based on the subunit recombinant envelope concept and produced in mammalian cells have been shown to protect chimpanzees from HIV-1 infection and to be safe and reasonably immunogenic in humans, inducing neutralizing antibodies. A second generation of candidate vaccines, which are based on live vectors expressing the envelope and other HIV-1 genes, and which are capable of inducing CTLs are beginning to be evaluated in human trials. Newer generations of candidate vaccines now being mostly explored in animal experiments are using combinations of subunit recombinant proteins or live vectored vaccines with other immunogens, such as synthetic peptides or pseudovirions, or are based on more novel approaches, including nucleic acid immunization and perhaps whole-inactivated or live attenuated vaccines.

However, there is a clear need for immunogenic preparations incorporating antigens or antigen fragments from primary or clinical HIV isolates. These preparations will be useful as vaccine candidates, as antigens in diagnostic assays and kits and for the generation of immunological reagents for diagnosis of HIV and other retroviral disease and infection.

Particular prior art immunogenic preparations include non-infectious, non-replicating HIV-like particles. PCT applications WO 93/20220 published Oct. 14, 1993 and WO 91/05860 published May 2, 1990 (Whitehead Institute for Biomedical Research), teach constructs comprising HIV genomes having an alteration in a nucleotide sequence which is critical for genomic RNA packaging, and the production of non-infectious immunogenic HIV particles produced by expression of these constructs in mammalian cells.

PCT application WO 91/07425 published May 30, 1991 (Oncogen Limited Partnership) teaches non-replicating retroviral particles produced by coexpression of mature retroviral core and envelope structural proteins such that the expressed retroviral proteins assemble into budding retroviral particles. A particular non-replicating HIV-1 like particle was made by coinfecting mammalian host cells with a recombinant vaccinia virus carrying the HIV-1 gag and protease genes and a recombinant vaccinia virus carrying the HIV-1 env gene.

In published PCT application WO 91/05864 in the name of the assignee hereof (which is incorporated herein by reference thereto), and corresponding granted U.S. Pat. Nos. 5,439,809 and 5,571,712, there is described particular non-infectious non-replicating retrovirus-like particles containing at least gag, pol and env proteins in their natural conformation and encoded by a modified retroviral genome deficient in long terminal repeats and containing gag, pol and env genes in their natural genomic arrangement.

In WO 96/06177 and corresponding copending U.S. patent application Ser. No. 08/292,967 filed Aug. 22, 1994 (abandoned), assigned to the assignee hereof and the disclosures of which are incorporated herein by reference, there are described further mutations to the HIV genome of the constructs of U.S. Pat. Nos. 5,439,809 and 5,571,712 to reduce gag-dependent RNA packaging of the HIV-1 genome, to eliminate reverse transcriptase activity of the pol gene product, to eliminate integrase activity of the pol gene product and to eliminate RNAse activity of the pol gene product, through genetic manipulation of the gag and pol genes.

In the preferred vectors described in the aforementioned U.S. Pat. Nos. 5,439,809 and 5,571,712 and U.S. application Ser. No. 08/292,967, abandoned, a metallothionein promoter is employed, which requires the addition of an inducer for expression to be effected. The use of such promoters for commercial scale production of such HIV-like particles is impractical, in view of the cost of the heavy metals employed and the toxic effect of such heavy metals on the expression cells.

It is desirable, therefore, to employ a constitutive promoter for expression of the HIV-like particles. However, it has been found that substitution of a constitutive promoter, results in cell toxicity, limiting the useful period of induction of the HIV-like particles.

SUMMARY OF INVENTION

It has now been surprisingly found that, by effecting specific genetic modification to the HIV genome, as set forth herein, it is possible to effect long term constitutive expression of non-infectious, non-replicating, immunogenic HIV-like particles without causing any toxic effect on the mammalian cells expressing the particles.

In accordance with one aspect of the present invention, there is provided a nucleic acid molecule, comprising a modified HIV genome devoid of long terminal repeats and wherein vpr and tat sequences are functionally disabled and a constitutive promoter operatively connected to the modified HIV genome for constitutive expression of the modified genome to produce non-infectious, non-replicating and immunogenic HIV-like particles.

The vpr and tat sequences may be functionally disabled by the insertion of stop codons therein preventing expression of the respective encoded gene products.

The HIV genome may be further modified by replacing the signal peptide of gp120 by a gp120 expression enhancing sequence, specifically the signal peptide encoding sequence of glycoprotein D (gD) of herpes simplex virus (HSV).

In a preferred embodiment of the invention, the env gene in the nucleic acid molecule encodes a env gene product from a primary HIV-1 isolate.

In accordance with the aforementioned U.S. application Ser. No. 08/292,967, abandoned, (WO 96/06177), the HIV genome of the nucleic acid molecule may be further modified to effect reduction in gag-dependent RNA packaging of the gag gene product. Such reduction in gag-dependent RNA packaging of the gag gene product may be effected by replacing Cys 395 and Cys 395 of the gag gene product of HIV-1 LAI isolate, or the corresponding amino acids of another isolate, by serine.

In addition or alternatively, also in accordance with U.S. application Ser. No. 08/292,967, abandoned, (WO 96/06177), the HIV genome of the nucleic acid molecule may be further modified to substantially eliminate reverse transcriptase activity, integrase activity and RNAse activity. In this regard, a BalI-BalI portion of the pol gene may be deleted between nucleotides 2655 and 4507 of the LAI isolate of HIV-1 or the corresponding portion of the pol gene of another HIV-1 isolate.

The constitutive promoter employed herein may be the human immediate early cytomegalovirus promoter or any other convenient constitutive promoter of expression of the non-infectious, non-replicating immunogenic HIV-like particles in mammalian cells. An expression enhancing sequence may be provided between the promoter and the modified genomes. Such an expression enhancing sequence may be the human cytomegalovirus Intron A sequence.

For the purposes of expression of the HIV-like particles, the nucleic acid molecule provided herein may be incorporated into an expression vector, which may be one having the identifying characteristics of plasmid pCMVgDtat$^-$vpr$^-$, as described in detail below.

The present invention, in another aspect thereof, provides a method of obtaining a non-infectious, non-replicating, immunogenic HIV-like particle, which comprises incorporating into an expression vector a nucleic acid molecule comprising a modified HIV genome devoid of long terminal repeats and wherein vpr and tat sequences are functionally disabled and a constitutive promoter operatively connected to the modified HIV genome, introducing the expression vector into mammalian cells, and constitutively expressing the nucleic acid molecule in the cells to stably produce non-infectious, non-replicating, immunogenic HIV-like particles.

The nucleic acid molecule incorporated into the expression vector may have the various features discussed above with respect to the nucleic acid molecule aspect of the invention. In addition to constitutive expression, expression of the nucleic acid molecule may also be enhanced by employing chemical agents which enhance the specific promoter employed. The expression vector preferably is one having the identifying characteristics of plasmid pCMVgDtat$^-$vpr$^-$.

Such method enables the HIV-like particles to be produced over a long term without any adverse toxic effect on the mammalian cells. As seen below, applicants have maintained constitutive expression through more than 50 passages of the cells. The present invention extends to the non-infectious, non-replicating immunogenic HIV-like particles lacking Tat and Vpr and producible by the method aspect of the invention as well as immunogenic compositions comprising the same and methods of immunization using such compositions.

The non-infectious, non-replicating immunogenic HIV-like particles produced according to the procedure of the invention may be employed in immunogenic compositions, as described in the aforementioned U.S. Pat. Nos. 5,439,809 and 5,571,712 and U.S. patent application Ser. No. 08/292,967, abandoned (WO 96/06177), for inducing an immune response in a host.

Advantages of the present invention include the ability to effect long-term production of non-infectious, non-replicating immunogenic HIV-like particles, thereby providing an expression system for such particles which is more useful in commercial production of the HIV-like particles than the systems previously considered.

BRIEF DESCRIPTION OF DRAWINGS

FIG. 2A shows expression plasmid pCMVgDtat⁻vpr⁻ while

FIG. 3, comprising panels A, B and C, shows Western blot analysis of HIV virus-like particles expressed from a Vero cell line containing the expression vector pCMVgDtat⁻vpr⁻ (clone Vero-356) which was established after stable transfection of Vero cells. The Western blot analysis shows the continued stable production of HIV-like particles with increasing passage number, panels A (passages 14 to 18) and B (passages 46 to 51), and upregulation of particle production following induction with sodium butyrate (NaBu) alone or NaBu plus dexamethasone (Dexam), panel C.

GENERAL DESCRIPTION OF THE INVENTION

The present invention enables the long term constitutive expression of non-infectious, non-replicating immunogenic HIV-like particles to be achieved through genetic manipulation of the HIV-1 genome. As described above, the present invention uses a constitutive promoter which is coupled to a modified HIV genome lacking LTRs.

The HIV genome is modified to disable vpr and tat to prevent their expression. Such disabling may be achieved by the insertion of stop codons, including multiple stop codons, to prevent translation of the genes and thereby preventing the formation of Vpr and Tat. By disabling these genes and preventing their expression, any toxic effect of these gene products on the mammalian cells is eliminated and hence a long-term production of the HIV-like particles can be achieved.

In addition, it is preferred to replace the sequence encoding the endogenous gp120 signal peptide with a signal peptide which enhances expression of the gp120, for example, the signal peptide of glycoprotein D of the Herpes Simplex Virus.

Figure 1:
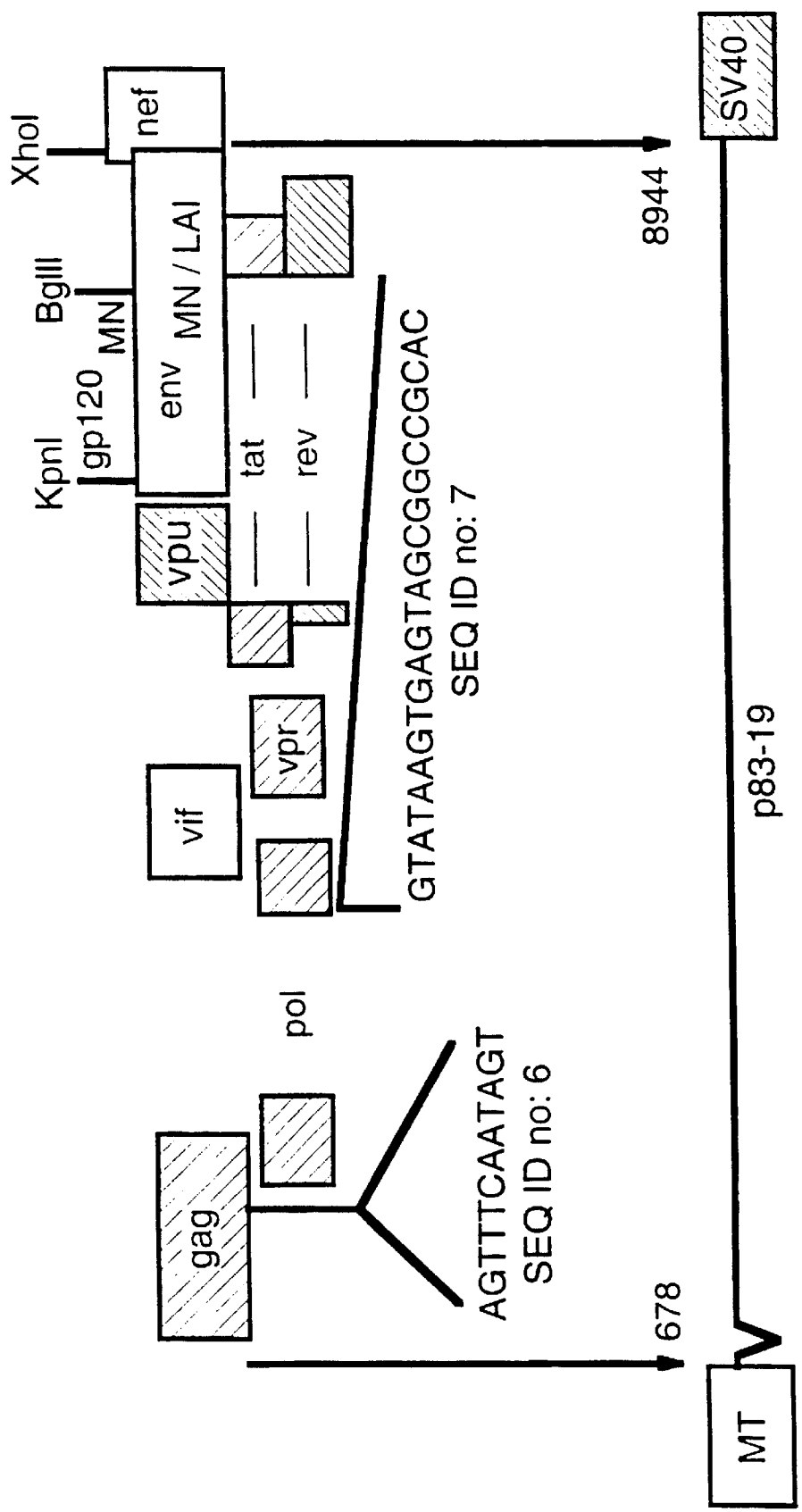
FIG. 1 shows the genetic map of expression plasmid p83-19 which contains a modified form of the 8.3 kb SacI-XhoI (nucleotides 678 to 8944) from the LAI HIV genome. The fragment lacks LTR elements and primer binding site and is inserted into an expression vector containing the metallothionein (MT) promoter and the SV40 virus polyadenylation site. The gag gene is modified to eliminate the RNA packaging sequences by replacing the codons encoding the two cysteine residues (Cys 392 and Cys 395) in the first Cys-His box by codons encoding serine. The pol gene has been modified by deletion of a portion to substantially remove the reverse transcriptase and integrase activities thereof. A oligonucleotide has been inserted within the deleted pol gene to introduce three stop codons in three different reading frames to prevent the remaining sequences of integrase from being translated. The env gene is a hybrid gene comprising the gp120 coding sequence of HIV-1 isolate MN and the gp41 coding sequence of isolate LAI.

An expression vector useful herein may be prepared by genetic modification of plasmid p83-19, shown in FIG. 1. This plasmid, the preparation of which is described in the aforementioned U.S. patent application Ser. No. 08/292,967, abandoned (WO 96/06177), encodes an HIV-like particle deficient in a plurality of elements required for infectivity and/or replication of HIV but dispensable for virus-like particle production. Plasmid p83-19 is derived from plasmid pMTHIVBRU described in the aforementioned U.S. Pat. Nos. 5,439,809 and 5,571,712. The HIV-like particle contains the env gene product which is substantially the envelope of HIV-1 isolate MN. The HIV-like particle may contain other env gene products, particularly those from clinical isolates from HIV-1 infected patients, such as a primary HIV-1 isolate from clades A, B, C, D, E and O, including the specific isolate Bx08. The env gene products also may be a chimer of the gp120 protein from one source and the gp41 from another source, such as MN/LAI, Bx08/LAI and clades/LAI chimers.

In the plasmid p83-19, the HIV genome comprises the SacI-XhoI restriction fragment of HIV-1 LAI isolate and encompasses nucleotides 678 to 8944 and is deficient in primer binding site. The gag gene has been modified to replace two cysteine residues ($Cys^{392}$ and $Cys^{395}$) in the gag gene product with serine, so as to inhibit RNA packaging. Furthermore, the pol gene has been modified to delete a large portion of the pol gene so as to remove the reverse transcriptase and integrase activities of the pol gene product, with an oligonucleotide sequence GTATAAGTGAG-TAGCGGCCGCAC (SEQ ID NO:7) being inserted within the reading frames to introduce stop codons to prevent the remaining sequences of integrase from being translated.

Figure 2A:
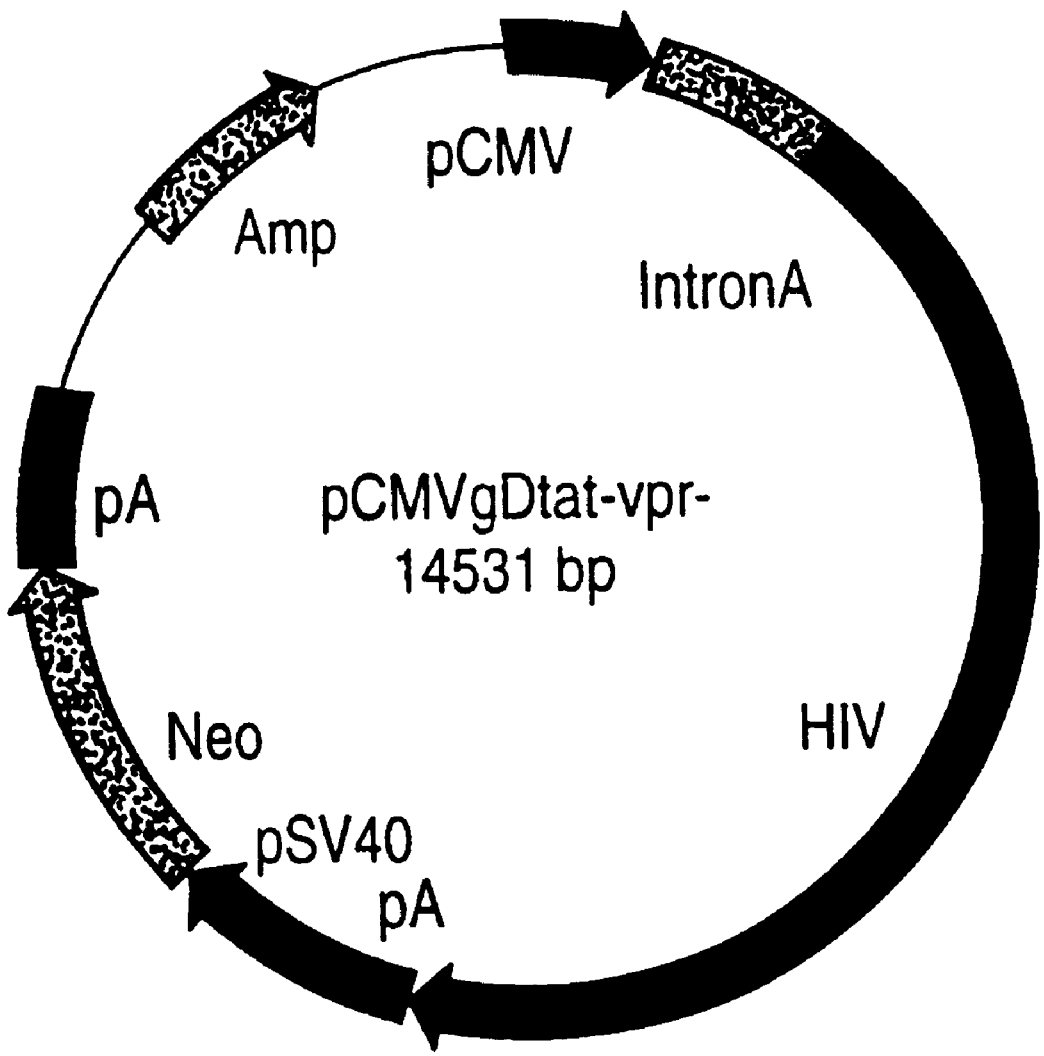
Figure 2B:
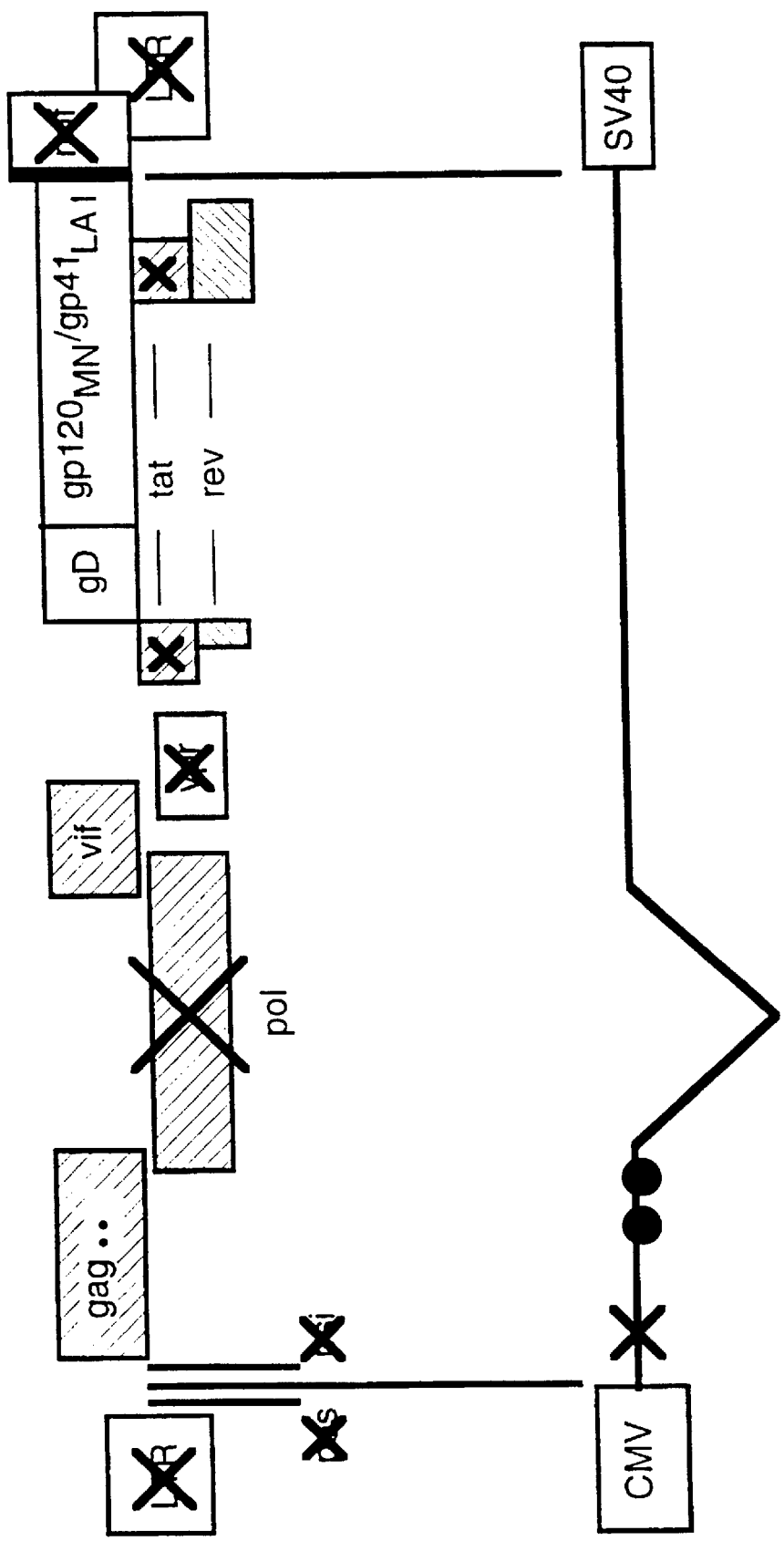
FIG. 2B shows the genetic map of the pCMV-pA segment of the expression plasmid. The expression plasmid pCMVgDtat⁻vpr⁻ is derived from plasmid p83-19 (FIG. 1) and contains the human cytomegalovirus (CMV) promoter and enhancer element as well as CMV Intron A sequences in place of the MT promoter. The coding sequences for the regulatory proteins Tat and Vpr were modified to prevent synthesis of both proteins upon expression. The signal peptide fragment of HIV-1 gp120 was replaced by the signal peptide fragment of the glycoprotein D (gD) of Herpes Simplex Virus (HSV). In addition, the G418 resistance gene was co-linearly inserted into the plasmid and placed under the regulation of the SV40 promoter and polyadenylation sequences.

The plasmid p83-19 is modified to provide plasmid pCMVgDtat⁻vpr⁻, a plasmid 14531 bp in length and the genetic elements and characteristics of which are shown in FIGS. 2A and 2B. The human metallothionein (MT) promoter present in p83-19 is replaced by the human immediate early cytomegalovirus (CMV) promoter and enhancer element. The signal peptide of gp120 is replaced by a sequence encoding the signal peptide fragment of glycoprotein D (gD) of Herpes Simplex Virus (HSV). This replacement is achieved by site directed mutagenesis, as described in Example 2 below, using specific primers.

The expression of the Tat protein is prevented by inserting stop codons at an appropriate site in the tat gene, specifically employing two stop codons (nucleotides TAATAG) replacing nucleotides TGGAAG (nucleotides 5896 to 5901) of HIV-$1_{LAI}$. Such mutation is effected by site directed mutagenesis, as described in Example 2 below, using a specific primer.

The expression of Vpr protein is prevented by inserting stop codons at an appropriate site in the vpr gene, specifically employing a stop codon (nucleotide TAG) at two different loci within the Vpr coding sequence, with the first stop codon replacing HIV-$1_{LAI}$ nucleotides 5625 to 5627 and the second stop codon replacing nucleotides 5631 to 5633.

Such mutation is effected by site-directed mutagenesis, as described in Example 2 below, using a specific primer.

A gene conferring resistance to G418 is colinearly inserted into the plasmid and placed under the regulation of SV40 promoter and polyadenylation sequences. The final plasmid assembly is shown in FIG. 2A.

The plasmid pCMVgDtat⁻vpr⁻ may be stably transfected into monkey kidney Vero cells or other mammalian cells by any convenient procedure for expression of non-infectious, non-replicating immunogenic HIV-like particles therefrom. G418 resistance cell lines are cloned and screened for production of the particles in the culture supernatant by measuring the amount of particle-associated Gag p24 protein using a suitable antibody. Such a screening procedure is described in the aforementioned U.S. Pat. Nos. 5,439,809 and 5,571,712.

Cell lines secreting the HIV-like particles were found to stably produce HIV-1-like particles and to continue to produce such HIV-like particles with increasing passage number, as may be seen from the Western blot analysis of FIG. 3. HIV-1-like particles can be isolated and analysed by Western blot using monoclonal antibodies specific for p24 (Gag) and gp120 (Env).

The levels of expression of the HIV-like particle may be increased by induction using sodium butyrate with or without dexamethasone, as seen from Example 3 and FIG. 3, panel C.

Since the genetic modifications which have been made to the HIV genome do not involve modification to immunogenic components of the HIV-like particle, the immunogenicity of the particles, as shown in U.S. Pat. Nos. 5,571,712 and 5,439,809 and U.S. application Ser. No. 08/292,967, abandoned, (WO 96/06177), is not impaired.

The non-infectious, non-replicating immunogenic HIV-like particles provided herein can be used in a variety of ways, as described in more detail below. The genetic modifications which have been made herein enable such HIV-like particles to be produced on a commercial scale from stably transformed cell lines expressing the particles in significant quantities, in contrast to prior art expression systems.

Vaccine Preparation and Use

One possible use of the non-infectious, non-replicating immunogenic HIV-like particles produced by the present invention is as the basis of a potential vaccine against retroviral diseases including AIDS and AIDS-related conditions.

Immunogenic compositions, suitable to be used as vaccines, may be prepared from the non-infectious, retrovirus-like particles. The immunogenic composition elicits an immune response which produces antibodies that are antiviral. Should the vaccinated subject be challenged by a retrovirus, such as HIV, the antibodies bind to the virus and thereby inactivate it. The immunogenic composition may also elicit cytotoxic T-lymphocytes (CTLs) which are able to lyse virally-infected cells.

Vaccines may be prepared as injectables, as liquid solutions or emulsions. The non-infectious HIV-like particles may be mixed with pharmaceutically-acceptable excipients which are compatible with the retrovirus-like particles. Excipients may include water, saline, dextrose, glycerol, ethanol, and combinations thereof. The vaccine may further contain auxiliary substances, such as wetting or emulsifying agents, pH buffering agents, or adjuvants to enhance the effectiveness of the vaccines. Methods of achieving an adjuvant effect for the vaccine include the use of agents, such as aluminum hydroxide or phosphate (alum), commonly used as 0.05 to 0.1 percent solution in phosphate buffered saline and other adjuvants, including QS21 and incomplete Freunds adjuvant. Vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as pharmaceutical grades of saccharine, cellulose and magnesium carbonate. These compositions take the form of solutions, suspensions, tablets, pills, capsules, sustained-release formulations or powders and contain 10 to 95% of the retrovirus-like particles of the invention.

The vaccines are administered in a manner compatible with the dosage formulation, and in such amount as is therapeutically effective, protective and immunogenic. The quantity to be administered depends on the subject to be treated, including, for example, the capacity of the individual's immune system to synthesize antibodies, and to produce a cell-mediated immune response. Precise amounts of active ingredient required to be administered depend on the judgement of the practitioner. However, suitable dosage ranges are readily determinable by one skilled in the art and may be of the order of micrograms of the HIV-like particles. Suitable regimes for initial administration and booster doses are also variable, but may include an initial administration followed by subsequent administrations. One example of an immunization schedule is at least one primary immunization with an HIV-like particle, produced according to the present invention, followed by at least one secondary immunization with a synthetic tandem T-B peptide containing a HIV T-cell epitope and a HIV B-cell epitope as described in European Patent No. 0 470 980 and corresponding copending U.S. patent application Ser. No. 07/768,608 filed May 3, 1990, abandoned, or WO 94/29339 and corresponding U.S. Pat. No. 5,639,854, assigned to the assignee hereof and the disclosures of which are incorporated herein by reference. The dosage of the vaccine may also depend on the route of 30 administration and will also vary according to the size of the host.

Molecules produced in accordance with the invention may further find use in the treatment (prophylactic or curative) of AIDS and related conditions, by acting either to displace the binding of the HIV virus to human or animal cells or by disturbing the 3-dimensional organization of the virus.

Immunoassays

The HIV-like particles produced by the method of the present invention are useful as immunogens, as antigens in immunoassays including enzyme-linked immunosorbent assays (ELISA), RIAs and other non-enzyme linked antibody binding assays, or procedures known in the art for screening anti-retroviral compounds, for the detection of anti-retroviral (for example, HIV) HIV antibodies and retroviral antigen (for example, HIV). In ELISA assays, the retrovirus-like particles are immobilized onto a selected surface, for example a surface capable of binding proteins, such as the wells of a polystyrene microtitre plate. After washing to remove incompletely adsorbed retrovirus-like particles, a non-specific protein, such as a solution of bovine serum albumin (BSA) or casein, that is known to be antigenically neutral with regard to the test sample may be bound to the selected surface. This allows for blocking of non-specific adsorption sites on the immobilizing surface and thus decreases the background caused by non-specific bindings of antisera onto the surface.

The immobilizing surface is then contacted with a sample, such as clinical or biological materials to be tested, in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution, such as PBS/Tween, or a borate buffer.

Following formation of specific immunocomplexes between the test sample and the bound retrovirus-like particles, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity, such as an enzymatic activity that will generate, for example, a colour development upon incubating with an appropriate chromogenic substrate. Quantification may then be achieved by measuring the degree of colour generation using, for example, a visible spectra spectrophotometer.

In one diagnostic embodiment where it is desirable to identify antibodies that recognize a plurality of HIV isolates, a plurality of antigenically-distinct HIV-like particles of the present invention are immobilized onto the selected surface. Alternatively, when the anti-HIV antibodies recognize epitopes that are highly conserved among various HIV isolates (for example, a B-cell epitope from gag or gp41) a single or a limited number of retrovirus-like particles may be immobilized. In a further diagnostic embodiment where it is desirable to specifically identify antibodies that recognize a single HIV isolate (for example, LAI, MN, SF2 or HXB2), a single particular HIV-like particle of the present invention may be immobilized. This further diagnostic embodiment has particular utility in the fields of medicine, clinical trials, law and forensic science where it may be critical to determine the particular HIV isolate that was responsible for the generation of an immune response including an antibody response.

In a further diagnostic embodiment, it may be desirable to specifically identify immunologically distinct retroviruses, for example, HIV isolates that belong to different clades. Immunologically distinct HIV isolates may include, for example, LAI, MN, SF2, HXB2 or a primary HIV-1 isolate. In this diagnostic embodiment, a particular HIV-like particle of the present invention is useful for generating antibodies including monoclonal antibodies that specifically recognize such an immunologically-distinct HIV isolate.

It is understood that a mixture of immunologically distinct HIV-like particles may be used either as an immunogen in, for example, a vaccine or as a diagnostic agent. There may be circumstances where a mixture of HIV-like particles are used to provide cross-isolate protection and/or diagnosis. In this instance, the mixture of immunogens is commonly referred to as a "cocktail" preparation.

The present invention advantageously provides HIV-like particles comprising gag and env gene products substantially in their native conformations. Such retrovirus particles will thus be recognized by conformational anti-HIV antibodies (such as anti-env antibodies) that may not recognize the HIV antigen in a denatured form or a synthetic peptide corresponding to such an HIV antigen. The HIV-like particles are, therefore, particularly useful as antigens and as immunogens in the generation of anti-retroviral antibodies (including monoclonal antibodies) in diagnostic embodiments.

Other Uses

Molecules which bind to the HIV-like particles, particularly antibodies, antibody-related molecules and structural analogs thereof, are also of possible use as agents in the treatment and diagnosis of AIDS and related conditions.

Variants of antibodies (including variants of antigen binding site), such as chimeric antibodies, humanized antibodies, veneered antibodies, and engineered antibodies that are specific for the retrovirus-like particles are included within the scope of the invention.

Antibodies and other molecules which bind to the HIV-like particles can be used for therapeutic (prophylactic and curative) and diagnostic purposes in a number of different ways, including the following:

For passive immunization by suitable administration of antibodies, possibly humanized antibodies, to HIV infected patients.

To activate complement or mediate antibody dependent cellular cytotoxicity (ADCC) by use of antibodies of suitable subclass or isotype (possibly obtained by appropriate antibody engineering) to be capable of performing the desired function.

For targeted delivery of toxins or other agents, for example, by use of immunotoxins comprising conjugates of antibody and a cytotoxic moiety, for binding directly or indirectly to cell-surface exposed HIV proteins of HIV-infected cells (for example, gp120).

For targeted delivery of highly immunogenic materials to the surface of HIV-infected cells, leading to possible ablation of such cells by either the humoral or cellular immune system of the host.

For detection of HIV, using a variety of immunoassay techniques.

Thus, in yet a further diagnostic embodiment of the invention, the immunogenic compositions (individually, or as mixtures including cocktail preparations) are useful for the generation of HIV antigen specific antibodies (including monoclonal antibodies) that can be used to detect HIV or antigens, or neutralize HIV in samples including biological samples.

In an alternative diagnostic embodiment, the HIV-like particles can be used to specifically stimulate HIV specific T-cells in biological samples from, for example, HIV-infected individuals for diagnosis or therapy.

Biological Deposits

Certain plasmids that encode HIV-like particles and are employed in aspects of the present invention that are described and referred to herein have been deposited with the American Type Culture Collection (ATCC) located at 10801 University Boulevard, Manassas, Va. 20110-2209, USA, pursuant to the Budapest Treaty and prior to the filing of this application. Samples of the deposited plasmids will become available to the public upon grant of a patent based upon this United States patent application and all restrictions imposed on access to the deposit will be removed. Deposits will be replaced if the depository is unable to dispense viable samples. The invention described and claimed herein is not to be limited in scope by the plasmids deposited, since the deposited embodiment is intended only as an illustration of the invention. Any equivalent or similar plasmids that encode similar or equivalent HIV-like particles as described in this application are within the scope of the invention.

Deposit Summary

| Plasmid | ATCC Designation | Date Deposited |
|---------|------------------|----------------|
| pMTHIVBRU | 75852 | Aug. 4, 1994 |
| pCMVgDtat⁻vpr⁻ | 209446 | Nov. 11, 1997 |

EXAMPLES

The above disclosure generally describes the present invention. A more complete understanding can be obtained by reference to the following specific Examples. These Examples are described solely for purposes of illustration and are not intended to limit the scope of the invention. Although specific terms have been employed herein, such terms are intended in a descriptive sense and not for purposes of limitations. Immunological and recombinant DNA methods may not be explicitly described in this disclosure but are well within the scope of those skilled in the art.

Example 1

This Example describes the construction of plasmid p83-19.

Plasmid p83-19 was constructed as described in the aforementioned U.S. patent application Ser. No. 08/292,967 (WO 96/06177) from pMTHIVBRU (ATCC 75852) as shown in FIG. 3 thereof. pMTHIVBRU is described in the aforementioned U.S. Pat. Nos. 5,439,809 and 5,571,712. Plasmid p83-19 contains a hybrid envelope gene which was engineered by replacing DNA encoding most of $gp120_{LAI}$ with the conjugate DNA encoding $gp120_{MN}$. This result was accomplished by replacing a KpaI/BglII DNA fragment (nucleotides 6379 to 7668) from HIV-$1_{LAI}$ with KpnI/BglII DNA fragment (nucleotides 6358 to 7641) from HIV-$1_{MN}$. The genetic map for plasmid p83-19 is shown in FIG. 1.

Example 2

This Example describes the construction of plasmid pCMVgDtat⁻vpr⁻.

Plasmid pCMVgDtat⁻vpr⁻ was constructed from plasmid p83-19, (Example 1). The human metallothionein promoter from p83-19 was replaced with the human cytomegalovirus (CMV) promoter and enhancer element as well as CMV Intron A sequences. The CMV sequences that were used correspond to a SspI-PstI DNA fragment (nucleotides 460 to 2087) described in ref. 9. The signal peptide fragment from HIV-1 gp120 was replaced by the signal peptide fragment of the glycoprotein D (gD) of Herpes Simplex Virus (HSV). This was accomplished by gene assembly-aided mutagenesis (GAAM), as previously described (ref. 10).

Three oligonucleotides were synthesized: an upstream primer having the sequence 5'-TATGACGACAAACAAAATCACGGCCCCCAACCTG GCGGCAGTCCCCCCCATTGCCACTGTCTTCTGCTCT TTCTATTA-3'(SEQ ID NO: 1), in which the last 27 nucleotides are complementary to nucleotides 6230 to 6256 of HIV-$1_{LAI}$, (all nucleotide numbering is according to ref. 11 and HIV Los Alamos Database, 1988); a downstream primer having the sequence 5'-CCCATAATAGACTGTGACCCACAATTTTTCTGTGA GAGAGGCATCCGCCAAGGCATATTTGCCGCGGACC CCATGGAGGCCCAC-3' (SEQ ID NO:2), in which the first 33 nucleotides are complementary to nucleotides 6347 to 6379 of HIV-$1_{LAI}$; a bridging oligonucleotide having the sequence 5'-TTGTTTGT CGTCATAGTGGGCCTCCATGGG-3' (SEQ ID NO:3), in which the first 15 oligonucleotides are complementary to the 5'-end 15 nucleotides of the upstream oligonucleotide while the last 15 nucleotides are complementary to the 3'-end 15 nucleotides of the downstream primer.

The expression of most of the Tat protein was prevented by inserting two stop codons (nucleotides TAATAG) which replaced nucleotides TGGAAG (nucleotides 5896 to 5901) of HIV-$1_{LAI}$. This mutation was generated by site-directed mutagenesis using the following oligonucleotide: 5'-GACTTCCTGGATGCTATTAGGGCTCTAGTCTAG-3' (SEQ ID NO:4). The expression of most of the Vpr protein was prevented by inserting a stop codon (nucleotides TAG) at two different loci within the Vpr coding sequences. The first stop codon replaced HIV-$1_{LAI}$ nucleotides 5625 to 5627 while the second stop codon replaced nucleotides 5631 to 5633. These mutations were inserted by site-directed mutagenesis using the following oligonucleotide: 5'-AAGACCAAGGGCCATAGAGGTAGCCACACAATG AA-3' (SEQ ID NO: 5). Finally, the gene conferring resistance to G418 was co-linearly inserted into the same plasmid and replaced under the regulation of the SV40 promoter and polyadenylation sequences. A map of the resulting plasmid pCMVgDtat⁻vpr⁻ is shown in FIG. 2A while details of the genomic modifications are shown in FIG. 2B.

Example 3

This Example illustrates the constitutive expression of HIV-1-like particles from a Vero cell clone established after stable transfection with plasmid pCMVgDtat⁻vpr⁻.

Plasmid pCMVgDtat⁻vpr⁻ prepared as described in Example 2, was stably transfected into monkey kidney Vero cells by the transfinity (BRL) calcium phosphate procedure. Approximately 400 stable G418$^R$ cell lines were cloned and screened for production of HIV-1-like particles by measuring the amount of particle-associated Gag p24 protein in the culture supernatants, as described in U.S. Pat. Nos. 5,439,809 and 5,571,712. One cell line secreting about 50 ng/ml of p24 was identified (clone Vero-356) and found to stably produce HIV-1-like particles with increasing passage number, as illustrated in FIG. 3, panels A and B. HIV-1-like particles were isolated by ultracentrifugation, and pelleted particles were analysed by Western Blot as described in U.S. application Ser. No. 08/292,967 (WO 96/06177) using monoclonal antibodies specific for p24 (anti-p24) and gp120 (Mab 50.1) (FIG. 3, panels A and B). The Western blot analysis shows continued production of HIV-like particles after over fifty passages, in considerable contrast to the results previously achieved.

The levels of particle production were increased three-fold by inducing clone Vero-356 with 5 mM sodium butyrate (NaBu), and five- to eight-fold by inducing the cell line with a mixture of 5 mM NaBu and 400 ng/ml dexamethasone (Dexam) (FIG. 3, panel C).

SUMMARY OF THE DISCLOSURE

In summary of the disclosure, the present invention provides a novel procedure for the preparation of non-infectious, non-replicating immunogenic HIV-like particles by constitutive expression by eliminating elements which are toxic to the mammalian cells and nucleic acid molecules useful in such procedure. Modifications are possible within the scope of the invention.

REFERENCES

1. World Health Organization, 1996. Wkly Epidemiol. Rec. 48:361.
2. Haynes B. F., Pantaleo G., Fauci A. S. 1996. Science 271:324–328.
3. Bryson Y. T., Pang S., Wei L. S. et al. 1995. N. Engl. J. Med. 332:833–834.
4. Rowland-Jones s., Sutton J., Ariyosh K., et al. 1995. Nat. Med. 1:59–64.
5. Pincus S., Messer K. G., Nara T. L., et al. 1994. J. Clin. Invest. 93:2508–2513.
6. Hogervorst E., Jurrians S., de Wolf F., et al. 1995. J. Infect. Dis. 171:811–821.
7. Markham R. B., Coberly J., Ruff A. J., et al. 1994. Lancet 343:1364.
8. Moore J. P. 1995. Nature 376:115.
9. Chapman, B. S. et al. 1991. Nucleic Acids Res. 19:3979–3986.
10. Yao F-L., Klein M. H., Loosmore S., Rovinski B. 1995. Bio Techniques 18:372–376.
11. Wain-Hobson S., Sonigo P., Danos O., Cole S., Alizon M. 1985. Cell 40:9–17.

What we claim is:

1. A nucleic acid molecule, comprising a modified HIV genome devoid of long terminal repeats and wherein vpr and tat sequences are functionally disabled by the insertion of stop codons therein preventing expression of the respective encoded gene products and the signal peptide encoding sequence of gp120 is replaced by the signal peptide encoding sequence of glycoprotein D of herpes simplex virus and a constitutive promoter operatively connected to said modified HIV genome for constitutive expression of said modified genome to produce non-infectious, non-replicating and immunogenic HIV-like particles.

2. The nucleic acid molecule of claim 1 wherein an env gene of said modified HIV genome encodes an env gene product from a primary HIV-1 isolate.

3. The nucleic acid molecule of claim 1 wherein said modified HIV genome is further modified to effect reduction in gag-dependent RNA packaging of the gag gene product.

4. The nucleic acid molecule of claim 1 wherein said modified HIV genome is further modified to substantially eliminate reverse transcriptase activity, integrase activity and RNAse activity.

5. The nucleic acid molecule of claim 1 wherein the constitutive promoter is the human immediate early cytomegalovirus promoter.

6. An expression vector comprising the nucleic acid molecule of claim 1.

7. The nucleic acid molecule of claim 3 wherein said reduction on gag-dependent RNA packaging of the gag gene product is effected by replacing Cys 392 and Cys 395 of the gag gene product of HIV-1 LAI isolate, or the corresponding amino acids of another HIV isolate, by serine.

8. The nucleic acid molecule of claim 4 wherein a BalI-BalI portion of pol gene is deleted between nucleotides 2655 and 4507 of the LAI isolate of HIV-1 or the corresponding portion of the pol gene of another HIV-1 isolate.

9. The nucleic acid molecule of claim 5 wherein an expression enhancing sequence is provided between said promoter and said modified genome.

10. The nucleic acid molecule of claim 9 wherein said expression enhancing sequence is the human cytomegalovirus Intron A sequence.

11. A method of obtaining a non-infectious, non-replicating, immunogenic HIV-like particle, which comprises:

incorporating into an expression vector a nucleic acid molecule comprising a modified HIV genome devoid of long terminal repeats and wherein vpr and tat sequences re functionally disabled by the insertion of stop codon therein preventing expression of the respective encoded gene products and the signal peptide encoding sequence of gp120 is replaced by the signal peptide encoding sequence of glycoprotien D of herpes complex virus and a constitutive promoter operatively connected to said modified HIV genome, introducing the expression vector into mammalian cells, and constitutively expressing the nucleic acid molecule in said cells to stably produce non-infectious, non-replicating, immunogenic HIV-like particles.

12. The method of claim 11 wherein the env gene encodes an env gene product from a primary HIV-1 isolate.

13. The method of claim 11 wherein said HIV genome is further modified to effect reduction in gag-dependent RNA packaging of the gag gene product.

14. The method of claim 11 wherein said HIV genome is further modified to substantially eliminate reverse transcriptase activity, integrase activity and RNAse activity.

15. The method of claim 11 wherein the constitutive promoter is the human immediate early cytomegalovirus promoter.

16. A non-infectious, non-replicating immunogenic HIV-like particle lacking Tat and Vpr and produced by the method of claim 11.

17. The method of claim 13 wherein said reduction in gag-dependent RNA packaging of the gag gene product is effected by replacing Cys 392 and Cys 395 of the gag gene product of HIV-1 LAI isolate, or the corresponding amino acids of another HIV isolate, by serine.

18. The method of claim 14 wherein a BalI-BalI portion of the pol gene is deleted between nucleotides 2655 and 4507 of the LAI isolate of HIV-1 or the corresponding portion of the pol gene of another HIV-1 isolate.

19. The method of claim 15 wherein an expression enhancing sequence is provided between said promoter and said modified genome.

20. The method of claim 19 wherein said expression enhancing sequence is the human cytomegalovirus Intron A sequence.

21. The method of claim 20 wherein expression of the nucleic acid molecule also is induced.

22. An immunogenic composition, comprising the non-infectious, non-replicating immunogenic HIV-like particle claimed in claim 16 and a physiologically-acceptable carrier therefor.

* * * * *

```
                            SEQUENCE LISTING

<160> NUMBER OF SEQ ID NOS: 7

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence: Synthetic

<400> SEQUENCE: 1
tatgacgaca aacaaaatca cggcccccaa cctggcggca gtcccccccca ttgccactgt      60 cttctgctct ttctatta                                                    78

<210> SEQ ID NO 2
<211> LENGTH: 84
<212> TYPE: DNA
<213> ORGANISM: Artificial Sequence
<220> FEATURE:
<223> OTHER INFORMATION: Description of Artificial Sequence: Synthetic

<400> SEQUENCE: 2
cccataatag actgtgaccc acaatttttc tgtgagagag gcatccgcca aggcatattt      60
gccgcggacc ccatggaggc ccac                                             84

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 3
ttgtttgtcg tcatagtggg cctccatggg                                       30

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 4
gacttcctgg atgctattag ggctctagtc tag                                   33

<210> SEQ ID NO 5
<211> LENGTH: 35
```

-continued

```
<212> TYPE: DNA
<213> ORGANISM: Artificial Sequence
<220> FEATURE:
<223> OTHER INFORMATION: Description of Artificial Sequence: Synthetic

<400> SEQUENCE: 5
aagaccaagg gccatagagg tagccacaca atgaa                              35

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 6
agtttcaata gt                                                       12

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 7
gtataagtga gtagcggccg cac                                           23
```